(12) United States Patent
Habig et al.

(10) Patent No.: US 11,672,962 B2
(45) Date of Patent: Jun. 13, 2023

(54) TUBE WITH APPLICATION TIP

(71) Applicant: BAYER ANIMAL HEALTH GMBH, Leverkusen (DE)

(72) Inventors: Jörg Habig, Cologne (DE); Wilfried Hinxlage, Dinklage (DE)

(73) Assignee: Bayer Animal Health GmbH, Monheim am Rhein (DE)

( * ) Notice: Subject to any disclaimer, the term of this patent is extended or adjusted under 35 U.S.C. 154(b) by 124 days.

(21) Appl. No.: 15/320,946

(22) PCT Filed: Jul. 17, 2015

(86) PCT No.: PCT/EP2015/066376
§ 371 (c)(1),
(2) Date: Dec. 21, 2016

(87) PCT Pub. No.: WO2016/012355
PCT Pub. Date: Jan. 28, 2016

(65) Prior Publication Data
US 2017/0197069 A1 Jul. 13, 2017

(30) Foreign Application Priority Data

Jul. 22, 2014 (EP) .................................... 14177936

(51) Int. Cl.
*A61M 35/00* (2006.01)
*A61M 31/00* (2006.01)
*B65D 35/38* (2006.01)

(52) U.S. Cl.
CPC .......... *A61M 35/003* (2013.01); *A61M 31/00* (2013.01); *B65D 35/38* (2013.01); *A61M 2207/00* (2013.01)

(58) Field of Classification Search
CPC ... A61J 1/067; A61J 1/062; A61J 1/18; B65D 1/095; B65D 1/0238; B65D 47/10;
(Continued)

(56) References Cited

U.S. PATENT DOCUMENTS 2,663,461 A * 12/1953 Brown .................. B65D 75/48
                                                     206/820
3,949,871 A    4/1976 Christensen et al.
(Continued)

FOREIGN PATENT DOCUMENTS

DE           44 20 594       12/1995
DE       202013103549 U1    10/2013
(Continued)

OTHER PUBLICATIONS

"Stitch Welding vs. Seam Welding." Fairlawn Tool, Inc. <https://www.fairlawntool.com/blog/stitch-welding-vs-seam-welding>. Accessed Oct. 6, 2022. (Year: 2016).*
(Continued)

*Primary Examiner* — Scott J Medway
(74) *Attorney, Agent, or Firm* — McBee Moore & Vanik IP, LLC

(57) ABSTRACT

The invention relates to a tube with an application tip for liquid or pasty material, in particular pharmaceutical. The tube has a tube body with an end which can be closed or has already been closed and with an outlet end. The outlet end of the tube has a tube neck with an outlet opening. Furthermore, the tube according to the invention has an application tip which is elongated in the longitudinal direction of the tube, is connected to the outlet end of the tube, and has an inner channel which connects an inlet opening and an application opening. A closure which closes the application opening is moulded onto the application opening of the application tip. The application tip has a gripping means.

17 Claims, 1 Drawing Sheet

(58) Field of Classification Search
CPC .... B65D 75/5811; B65D 35/08; B65D 47/36; B65D 17/06; B65D 41/32; B65D 2221/00; A61M 35/003
See application file for complete search history.

(56) References Cited

U.S. PATENT DOCUMENTS

| | | | | |
|---|---|---|---|---|
| 3,993,223 | A * | 11/1976 | Welker, III | B65D 1/095 222/107 |
| 4,055,282 | A * | 10/1977 | Komendowski | B65D 1/0238 222/421 |
| 4,207,990 | A * | 6/1980 | Weiler | A61J 1/1406 215/375 |
| 4,284,213 | A * | 8/1981 | Lee | B65D 47/10 220/266 |
| D269,706 | S * | 7/1983 | Green | D24/115 |
| 4,402,420 | A * | 9/1983 | Chernack | A61J 1/1412 220/266 |
| D274,754 | S * | 7/1984 | Chernack | D24/129 |
| 4,458,818 | A * | 7/1984 | Hansen | B65D 1/0238 215/245 |
| 4,512,475 | A * | 4/1985 | Federighi | A61J 1/067 206/484 |
| 4,529,095 | A * | 7/1985 | Hansen | B65D 23/00 215/331 |
| 4,620,638 | A * | 11/1986 | Schmidt | B65D 1/0238 215/11.1 |
| 4,643,309 | A * | 2/1987 | Evers | B65D 1/0238 206/484 |
| D304,683 | S * | 11/1989 | Hofer | D9/538 |
| 5,006,004 | A * | 4/1991 | Dirksing | A45D 19/02 401/261 |
| 5,076,452 | A * | 12/1991 | Hashimoto | B65D 1/0238 215/388 |
| 5,188,250 | A * | 2/1993 | Kovacic | A61J 1/067 215/48 |
| 5,244,120 | A * | 9/1993 | O'Meara | B65D 35/22 222/94 |
| D347,390 | S * | 5/1994 | Kovacic | D9/539 |
| D367,613 | S * | 3/1996 | Weiler | D24/224 |
| 5,678,736 | A | 10/1997 | Hansen | |
| 5,878,900 | A * | 3/1999 | Hansen | B65D 1/0238 215/50 |
| 5,901,865 | A * | 5/1999 | Weiler | B65D 23/003 215/48 |
| 5,908,124 | A * | 6/1999 | Klauke | B65D 1/0238 215/42 |
| 6,116,449 | A * | 9/2000 | Chiesi | B65D 1/095 220/23.4 |
| D463,290 | S * | 9/2002 | Wiggins | D9/557 |
| D467,336 | S * | 12/2002 | Gilbard | D24/115 |
| 6,543,655 | B1 * | 4/2003 | de Laforcade | B65D 47/36 222/541.9 |
| 6,595,969 | B1 | 7/2003 | Emerit et al. | |
| 6,874,665 | B2 * | 4/2005 | Doherty | B65D 1/095 222/541.5 |
| 6,892,906 | B2 | 5/2005 | Py et al. | |
| 6,991,140 | B2 * | 1/2006 | Bourque | B65D 47/148 215/48 |
| 7,487,894 | B2 * | 2/2009 | Zahn | A61J 1/067 222/107 |
| D666,289 | S * | 8/2012 | DeCoste | D24/115 |
| 8,377,029 | B2 * | 2/2013 | Nagao | B65D 1/095 220/255 |
| 8,833,576 | B2 * | 9/2014 | Fontana | A61J 1/067 206/530 |
| D731,642 | S * | 6/2015 | Cehajic | B65D 1/095 D24/115 |
| 9,364,393 | B1 * | 6/2016 | Grabowski | A61J 1/067 |
| 9,988,190 | B2 * | 6/2018 | Berg, Jr. | B65D 75/008 |
| 11,090,260 | B2 * | 8/2021 | Todd | A61M 31/00 |
| 2005/0096610 | A1 * | 5/2005 | Marsden | A61M 35/003 604/295 |
| 2005/0098582 | A1 * | 5/2005 | Gomez | B65D 83/0072 222/206 |
| 2006/0108384 | A1 * | 5/2006 | Zahn | A61J 1/067 222/541.9 |
| 2006/0110208 | A1 * | 5/2006 | Tsaur | B65D 39/00 401/205 |
| 2007/0138215 | A1 | 6/2007 | Zahn et al. | |
| 2007/0228073 | A1 * | 10/2007 | Mazzarino | B65D 75/5811 222/107 |
| 2011/0160677 | A1 | 6/2011 | March | |
| 2013/0108352 | A1 | 5/2013 | Ruiz, Sr. et al. | |
| 2013/0345673 | A1 | 12/2013 | Ferreri et al. | |
| 2014/0094759 | A1 * | 4/2014 | Mansfield | A61F 9/0008 604/290 |
| 2018/0050859 | A1 * | 2/2018 | May | B65D 83/0005 |

FOREIGN PATENT DOCUMENTS

| | | | |
|---|---|---|---|
| EP | 0488710 A1 | 6/1992 | |
| EP | 1480886 A1 * | 12/2004 | ............... B65D 1/32 |
| JP | 2008521713 A | 6/2008 | |
| RU | 2248816 C2 | 3/2005 | |
| WO | WO 2006/058138 | 6/2006 | |

OTHER PUBLICATIONS

"Seamless welding process." Sunny Steel Enterprise Ltd. <https://www.sunnysteel.com/seamless-welding-process.php>. Accessed Oct. 6, 2022. (Year: 2022).*

"Weld." Merriam-Webster.com Dictionary, Merriam-Webster, <https://www.merriam-webster.com/dictionary/weld>. Accessed Oct. 6, 2022. (Year: 2022).*

"Seamless welding". Hunan Standard Steel Co. <https://www.hu-steel.com/rn/news355_480.html>. Accessed Oct. 6, 2022 (Year: 2022).*

International Search Report and Written Opinion of the ISA for PCT/EP2015/066376 dated Sep. 17, 2015, 15 pages.

Colombian Office Action dated Sep. 18, 2108 in CO application NC2017/0000053.

JP Office Action for App. 2017-524099 dated Oct. 5, 2020. Translation included.

* cited by examiner

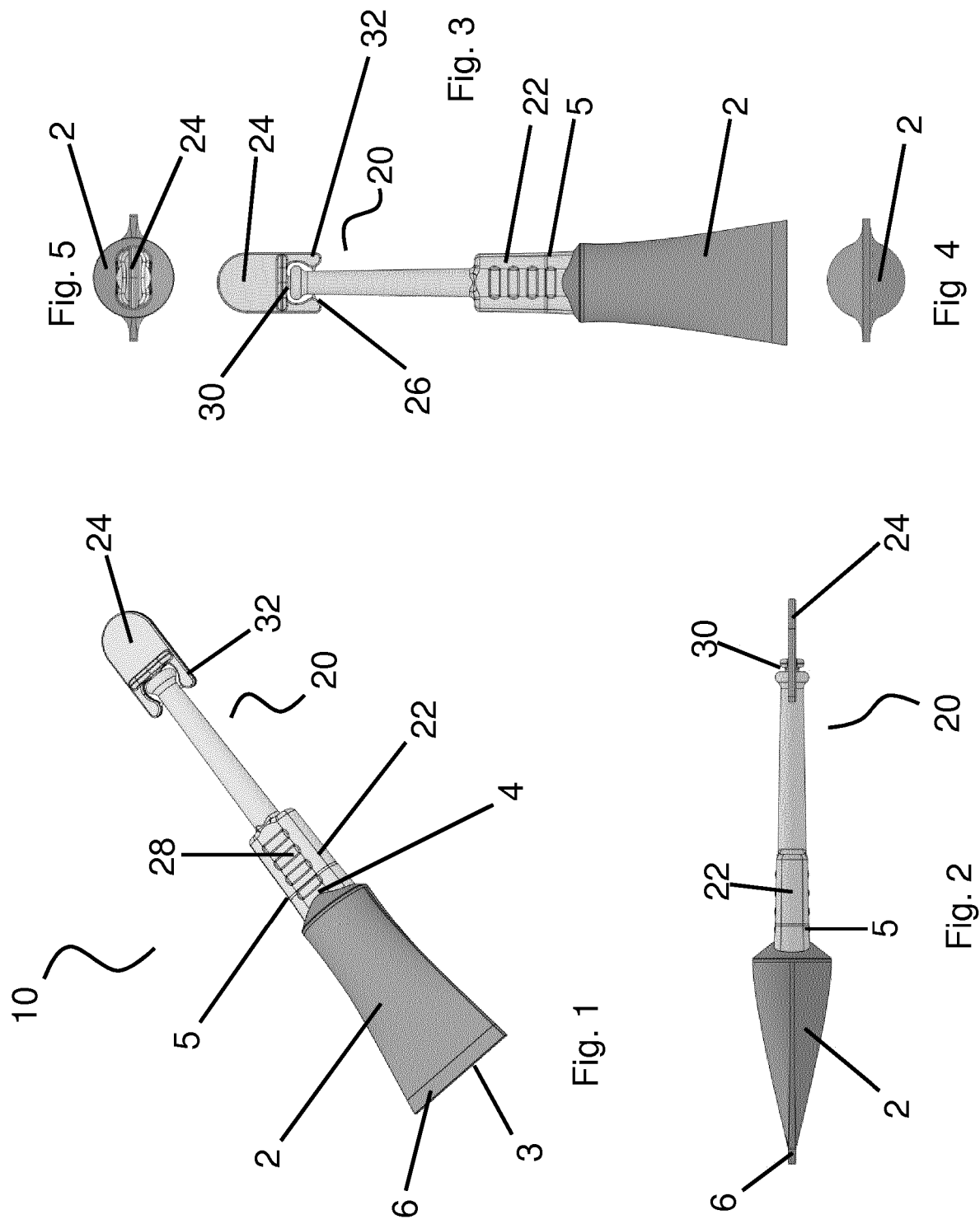

TUBE WITH APPLICATION TIP

This application is the U.S. national phase of International Application No. PCT/EP2015/066376 filed 17 Jul. 2015, which designated the U.S. and claims priority to EP Patent Application No. 14177936.3 filed 22 Jul. 2014, the entire contents of each of which are hereby incorporated by reference.

The invention relates to a tube with an application tip for liquid or pasty material, in particular an active agent formulation, and to a method for producing and filling the tube with an application tip. Tubes of this type preferably contain a single dose of an active agent formulation, for example of a pharmaceutical. The application tip serves to introduce the active agent into regions of the human and animal body which are difficult to access, such as body openings or the skin in regions of pronounced hairiness.

US 2011/0160677 A1 has disclosed a container for the application of a single dose of a liquid medicine into the oral cavity of a patient. The container has a chamber for receiving the liquid medicine and a squeezable region which is utilized to discharge the medicine. The container is sealed by way of a closure which can be twisted off, in order to prevent premature discharge of the medicine. Furthermore, the container has an elongated small dispensing tube which has a length of from 1 to 12 cm and is in fluidic connection with the chamber. In order to open the container, the user grips the container with one hand. With the thumb and forefinger of the other hand, the user grips the closure and exerts a rotational force on the closure, with the result that the seal breaks at a predetermined break point and the closure can be severed from the container. Apart from the single dose of liquid medicine, inert gas is situated inside the container, in order to prevent the liquid medicine from exiting the container as a result of the pressure which the user exerts on the container.

A container of similar design and handling is disclosed in US 2007/0138215 A1. Here too, the user grips the container with one hand. A special means for non-positive firm holding and pressing of the chamber with the liquid in the form of grooves and channels is provided on the outside of the chamber. The chamber is automatically gripped by the user in the region of the grooves and channels when the user wishes to open and twist off the closure which can be twisted off. In contrast to the container in US 2011/0160677 A1, this patent application does not disclose any measures as to how the escape of liquid as a result of the pressure on chambers filled with liquid during opening of the closure can be prevented.

A further container for flowable materials is known from DE 44 20 594 A1. The container from DE 44 20 594 A1 consists of a housing made from plastic, the head of which has a discharge opening, and an open chamber which adjoins the open end. The containers of this type serve to receive filling products. The contents can be removed from the container by way of manual pressing. The container is closed by means of a closure which can be severed along a predetermined break point by way of tilting or twisting of said closure relative to the container body. During opening of the described container according to DE 44 20 594 A1, the container body has to be held firmly with corresponding pressure. It is disadvantageous here that liquid can escape as a result of the pressure during opening of the closure.

The invention is based on the object of providing a tube with an application tip, the closure of which can be opened, without it being necessary in the process for the tube body to be held firmly and thus for pressure to be exerted on the tube body.

In the following text, tube means every type of squeezable container. According to the invention, this object is achieved by way of the tube with an application tip according to Claim 1 and the production method according to Claim 22.

The tube according to the invention with an application tip for liquid or pasty material, in particular a pharmaceutical, has a tube body with an end which can be closed or has already been closed and with an outlet end. The outlet end of the tube has a tube neck with an outlet opening. Furthermore, the tube according to the invention has an application tip which is elongated in the longitudinal direction of the tube, is connected to the outlet end of the tube and has an inner channel which connects an inlet opening and an application opening. A closure which closes the application opening is moulded onto the application opening of the application tip. The application tip has a gripping means.

In one embodiment of the invention, the application tip is moulded onto the tube neck, with the result that the outlet opening of the tube and the inlet opening of the channel are connected to one another in a liquid-tight manner.

The gripping means serves to provide a holding point during opening of the tube. The region of the gripping means is preferably of somewhat thicker configuration in terms of the material, for example is present by way of a corresponding reinforcement which does not yield upon pressure.

The application tip has the gripping means over its entire length or over a part region of its length. The gripping means can be configured as a widened portion (in one dimension) of the outer and optionally also the inner cross section of the application tip with respect to the outer or inner cross section in other part regions of the application tip. The application tip preferably has the gripping means in the region of the inlet opening. The gripping means can be configured as a recessed grip, preferably with grooves and ribs.

The application tip can be moulded onto the tube neck in a positively locking manner by way of welding.

The tube body and the application tip are produced from plastic, preferably from polypropylenes (PP). In other embodiments, however, they can also be produced from polyethylene (PE), polyethylene terephthalate (PET), polyvinyl chloride (PVC) or polyamide (PA). In one embodiment of the invention, the wall thickness of the application tip is greater than the wall thickness of the tube body. The wall thickness of the tube body can lie in the range from 0.2 mm to 0.6 mm and the wall thickness of the application tip can lie in the range from 0.3 to 1.2 mm. The wall thickness of the application tip can be greater in the region of the gripping means than in the remaining part regions of the application tip. The wall thickness in the region of the gripping means can be greater than the wall thickness of the remaining part regions of the application tip. It can lie in the range from 0.4 to 1.4 mm.

The length of the application tip without closure should be at least 20% of the length of the tube body, preferably at least 50% and particularly preferably greater than or equal to the length of the tube body. The length of the application tip without closure preferably lies in the range from 15 mm to 70 mm and the length of the tube body lies in the range from 15 mm to 70 mm.

In a further embodiment of the invention, the material of the application tip is transparent. The material of the tube body is preferably not transparent.

That end of the tube body which can be closed or has already been closed can be closed by way of transverse sealing.

The closure can be connected to the application tip via one or more predetermined break points. It can preferably be broken off from the application tip by bending or by twisting.

In one embodiment, the tube with an application tip contains a single dose of pharmaceutical formulation.

The channel in the application tip preferably has a diameter in the range from 0.5 to 0.8 mm.

A further subject matter of the invention is a method for producing a filled tube with an application tip, containing the steps
  a. forming of a tube body with an open end and an outlet end which has a tube neck with an outlet opening,
  b. forming of an application tip with an inner channel which connects an inlet opening and an application opening, and a closure which closes the application tip,
  c. moulding of the application tip with the region around its inlet opening onto the tube neck,
  d. filling of the tube body with a liquid or pasty material via the open end,
  e. transverse sealing of the open end.

FIGURES AND EXAMPLES

One exemplary embodiment of the invention is to be explained with reference to the figures of the drawing, in which:

FIG. 1 shows a tube with an application tip in a perspective view,

FIG. 2 shows a tube with an application tip in a side view,

FIG. 3 shows a tube with an application tip in a front view,

FIG. 4 shows a tube with an application tip from below, and

FIG. 5 shows a tube with an application tip from the top.

The tube with an application tip 10 depicted in FIGS. 1 to 5 consists of a tube body 2 in an application tip 20.

In the exemplary embodiment which is shown, the tube body 2 is closed at its end 3 by way of a transverse sealing seam 6. In order to make simple opening and application possible, the tube body 2 is provided with a long application tip 20 with a closure 24 which is easy to open and closes the application opening 30. The closure 24 can be broken off by twisting or by bending. The closure is connected to the wall of the application tip 20 by way of two extension pieces 32 which protrude beyond the application opening 30 in the direction of the tube body and via two predetermined break points 26 at the end of the extension pieces on opposite sides. The long application tip 20 serves, even in the case of regions which are difficult to access, for example in the animal fur or in body openings, to make an application of the tube contents possible without problems. The application tip 20 can be of transparent design, with the result that a discharge of the filling material can be seen.

The outlet end 4 of the tube with an application tip 10 has a tube neck 5 with an outlet opening (not visible here). The tube neck 5 which is visible merely faintly through the transparent application tip 20 is indicated by a line. The application tip 20 is moulded in a positively locking manner onto the tube neck 5. In the region of the inlet opening, with which it is also moulded onto the tube neck 5, the application tip 20 has a recessed grip 22 with transverse ribs 28, the recessed grip 22 going beyond the tube neck 5.

The invention claimed is:

1. A tube with an application tip for liquid or pasty material, in particular an active agent formulation, having
  a. a tube body with an end which can be closed or has already been closed and with an outlet end which has a tube neck with an outlet opening, said tube body having a wall,
  b. an application tip which is elongated in the longitudinal direction of the tube, is connected to the outlet end of the tube body and has an inner channel having an inlet opening and an application opening, said application tip having a first part region of its longitudinal length adjacent the inlet opening and a second part region of its longitudinal length adjacent the outlet opening, and said application tip having a wall enclosing the inner channel, and
  c. a closure which is moulded onto the application opening of the application tip and closes the application opening,
    wherein the application tip has a gripping means which extends over only the first part region of the application tip and is configured as a widened portion of an outer cross section of the application tip, wherein the widened portion is widened in a first dimension vertical to the longitudinal direction with respect to an outer cross section in the second part region of the application tip, and wherein the first and second part region have substantially the same outer cross section in a second dimension perpendicular to the first dimension,
    wherein the gripping means is configured as a recessed grip comprising transverse ribs at right angle to the longitudinal direction of the application tip, and
    wherein a wall thickness of the application tip is greater than a wall thickness of the tube body, and wherein the closure is connected to the wall of the application tip in the second part region by way of extension pieces which protrude beyond the application opening in the direction of the tube body and via predetermined break points at the end of the extension pieces, and wherein the closure is not in direct contact with the gripping means and does not overlap the gripping means, and
    wherein the application tip is moulded onto the tube neck in a positively locking manner by way of welding, and
    wherein the material of the application tip is transparent and the material of the tube body is not transparent.

2. The tube with an application tip of claim 1, wherein the application tip is moulded onto the tube neck, with the result that the outlet opening of the tube body and the inlet opening of the inner channel of the application tip are connected to one another in a liquid-tight manner.

3. The tube with an application tip of claim 1, wherein the gripping means is configured as a recessed grip, optionally with grooves and ribs.

4. The tube with an application tip of claim 1, wherein the tube body and the application tip are produced in each case from polypropylenes (PP).

5. The tube with an application tip of claim 1, wherein the tube body and the application tip are produced in each case from polyethylene (PE), polyethylene terephthalate (PET), polyvinyl chloride (PVC) or polyamide (PA).

6. The tube with an application tip of claim 1, wherein the wall of the tube body has a thickness that lies in the range from 0.2 mm to 0.6 mm.

7. The tube with an application tip of claim 1, wherein the wall of the application tip has a thickness that lies in the range from 0.3 mm to 1.2 mm.

8. The tube with an application tip of claim 3, wherein the wall of the application tip in the region of the recessed grip has a thickness that is higher than in the remaining part regions of the application tip and lies in the range from 0.4 mm to 1.4 mm.

9. The tube with an application tip of claim 1, wherein the length of the application tip without closure is at least 20% of the length of the tube body.

10. The tube with an application tip of claim 1, wherein the length of the application tip without closure lies in the range from 15 mm to 70 mm.

11. The tube with an application tip of claim 1, wherein the length of the tube body lies in the range from 15 mm to 70 mm.

12. The tube with an application tip of claim 1, wherein the end which can be closed or has already been closed can be closed or is closed by way of transverse sealing.

13. The tube with an application tip of claim 1, wherein the closure can be broken off by bending or by twisting.

14. The tube with an application tip of claim 1, wherein the tube with an application tip contains a single dose of pharmaceutical formulation.

15. The tube with an application tip of claim 1, wherein the channel has a diameter in the range from 0.5 mm to 0.8 mm.

16. The tube with an application tip of claim 1, wherein the length of the application tip without closure is at least 50% of the length of the tube body.

17. The tube with an application tip of claim 1, wherein the length of the application tip without closure is greater than or equal to the length of the tube body.

* * * * *